(12) United States Patent
Fujiwara

(10) Patent No.: US 9,829,460 B2
(45) Date of Patent: Nov. 28, 2017

(54) BIOSENSOR SYSTEM, SENSOR CHIP, AND METHOD OF MEASURING ANALYTE CONCENTRATION IN BLOOD SAMPLE

(71) Applicant: Panasonic Healthcare Holdings Co., Ltd., Tokyo (JP)

(72) Inventor: Masaki Fujiwara, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 209 days.

(21) Appl. No.: 14/568,889

(22) Filed: Dec. 12, 2014

(65) Prior Publication Data

US 2015/0168340 A1   Jun. 18, 2015

Related U.S. Application Data

(63) Continuation of application No. 12/935,803, filed as application No. PCT/JP2009/001560 on Apr. 2, 2009, now Pat. No. 8,940,138.

(30) Foreign Application Priority Data

Apr. 7, 2008   (JP) ................... 2008-099692

(51) Int. Cl.
   *C12Q 1/26*      (2006.01)
   *G01N 27/327*    (2006.01)
   (Continued)

(52) U.S. Cl.
   CPC .......... *G01N 27/3273* (2013.01); *C12Q 1/26* (2013.01); *G01N 27/3274* (2013.01)

(58) Field of Classification Search
   CPC ... C12Q 1/00; C12Q 1/26; C12Q 1/54; C12M 1/34; G01N 27/327; G01N 27/3272;
   (Continued)

(56) References Cited

U.S. PATENT DOCUMENTS 5,405,511 A   4/1995   White et al.
6,228,237 B1  5/2001   Goumont et al.
(Continued)

FOREIGN PATENT DOCUMENTS

CN   1839313    9/2006
EP   1 691 192  8/2006
(Continued)

*Primary Examiner* — Susan D Leong
(74) *Attorney, Agent, or Firm* — Hamre, Schumann, Mueller & Larson P.C.

(57) ABSTRACT

The present invention provides a biosensor system that can prevent a measurement error caused by the temperature of the environment in use from occurring. A biosensor system 100 includes a measuring instrument 101 having an operation part 306, and a sensor chip 200 that is insertable into and removable from the measuring instrument 101 and into which a blood sample is introduced. The sensor chip 200 includes a measurement part 41 (a measurement part A) that acquires Data a related to the concentration of an analyte in a blood sample based on the amount of electric current that flows in the blood sample due to a reaction in which an oxidoreductase with the analyte used as a substrate is involved, and a measurement part 42 (a measurement part B) that acquires, from the blood sample, Data b for temperature correction of Data a. The operation part 306 has a function of determining the concentration of the analyte in the blood sample, with the concentration having been corrected according to the temperature of the blood sample based on Data a and Data b.

7 Claims, 6 Drawing Sheets

(51) Int. Cl.
*G01N 33/48* (2006.01)
*C12Q 1/54* (2006.01)

(58) Field of Classification Search
CPC ........ G01N 33/49; G01N 33/80; G01N 33/26; A61B 5/150274; A61B 5/14535
See application file for complete search history.

(56) References Cited

U.S. PATENT DOCUMENTS

| | | |
|---|---|---|
| 6,780,296 B1 | 8/2004 | Bhullar et al. |
| 7,232,510 B2 | 6/2007 | Miyazaki et al. |
| 7,452,457 B2 | 11/2008 | Burke et al. |
| 7,510,643 B2 | 3/2009 | Bhullar et al. |
| 7,655,456 B2 | 2/2010 | Oshiman et al. |
| 2003/0159945 A1 | 8/2003 | Miyazaki et al. |
| 2004/0256248 A1 | 12/2004 | Burke et al. |
| 2005/0008537 A1* | 1/2005 | Mosoiu ............... G01N 33/558 422/400 |
| 2005/0070777 A1 | 3/2005 | Cho et al. |
| 2005/0145490 A1 | 7/2005 | Shinno et al. |
| 2006/0194336 A1 | 8/2006 | Tatebe et al. |
| 2007/0205114 A1* | 9/2007 | Mathur ............... G01N 27/3274 205/792 |
| 2008/0118984 A1 | 5/2008 | Yuan et al. |

FOREIGN PATENT DOCUMENTS

| | | |
|---|---|---|
| JP | 8-503304 | 4/1996 |
| JP | 2001-235444 | 8/2001 |
| JP | 2003-042995 | 2/2003 |
| JP | 2003-156469 | 5/2003 |
| JP | 2007-524826 | 8/2007 |
| WO | 03/062812 | 7/2003 |
| WO | 2004/113910 | 12/2004 |
| WO | 2007/100651 | 9/2007 |

* cited by examiner

|  |  | Data c (μA) | Data d (μA) |
|---|---|---|---|
| Glucose Concentration (mg/dl) | ⋮ | ⋮ | ⋮ |
| | 50 | 0.60 | 42.97 |
| | ⋮ | ⋮ | ⋮ |
| | 100 | 0.86 | 42.30 |
| | ⋮ | ⋮ | ⋮ |
| | 250 | 1.66 | 42.57 |
| | ⋮ | ⋮ | ⋮ |
| | 400 | 2.48 | 42.03 |
| | ⋮ | ⋮ | ⋮ |
| | 600 | 3.54 | 41.57 |
| | ⋮ | ⋮ | ⋮ |

Fig. 5

|  | Data d /Data c |
|---|---|
| Glucose Concentration (mg/dl) | ⋮ |
| 50 | 71.61 |
| ⋮ | ⋮ |
| 100 | 49.00 |
| ⋮ | ⋮ |
| 250 | 25.59 |
| ⋮ | ⋮ |
| 400 | 16.95 |
| ⋮ | ⋮ |
| 600 | 11.74 |
| ⋮ | ⋮ |

Fig. 6

BIOSENSOR SYSTEM, SENSOR CHIP, AND METHOD OF MEASURING ANALYTE CONCENTRATION IN BLOOD SAMPLE

TECHNICAL FIELD

The present invention relates to a biosensor system, a sensor chip, and a method of measuring the analyte concentration in a blood sample.

BACKGROUND ART

In order to measure the analyte concentration, for example, the blood glucose concentration (the blood glucose level), in a blood sample, a portable biosensor system is used that includes a measuring instrument with an operation part and a sensor chip that is insertable into and removable from the measuring instrument.

The concentration of an analyte is calculated based on the amount of an oxidant or a reductant that is generated by an enzyme cycling reaction. The reaction is carried out through an oxidoreductase, with the analyte used as a substrate. The rate of the enzyme cycling reaction depends on the temperature (the reaction temperature) at which the reaction is carried out. Therefore, it is desirable to correct the analyte concentration based on the reaction temperature.

As described in, for example, JP 2003-156469 A, the reaction temperature is measured with a temperature sensor disposed in the measuring instrument. In the biosensor system described in JP 2003-156469 A, however, since the internal temperature of the measuring instrument is measured, the reaction temperature measured therein does not reflect the temperature of the blood sample accurately. Accordingly, an error may be caused in the measurement of the analyte concentration.

JP 2001-235444 A, JP 2003-42995 A, and International Publication WO2003/062812 each disclose a biosensor system for improving the accuracy of measuring the reaction temperature. The biosensor systems described in JP 2001-235444 A and JP 2003-42995 A each include a thermally-conductive member in the vicinity of a blood sample holding part of a sensor chip and detect the temperature of the blood sample transmitted through the thermally-conductive member by a temperature sensor disposed in the measuring instrument. In the biosensor systems described in JP 2001-235444 A and JP 2003-42995 A, since a resin plate is disposed between the thermally-conductive member and the blood sample holding part, the thermally-conductive member does not come into contact with a blood sample. In the biosensor system described in International Publication WO2003/062812, a temperature sensor and a thermally-conductive member are disposed in the insertion part of the measuring instrument where a sensor chip is inserted and the temperature of the blood sample is transmitted to the temperature sensor through the thermally-conductive member.

CITATION LIST

Patent Literature

PTL 1: JP 2003-156469 A
PTL 2: JP 2001-235444 A
PTL 3: JP 2003-42995 A
PTL 4: International Publication WO2003/062812

SUMMARY OF INVENTION

Technical Problem

When a user carrying a biosensor system moves from one place to another that has a significant difference in temperature (for example, moves from outside to inside in winter or summer), the measuring instrument cannot follow the rapid change in environmental temperature and therefore has a higher or lower temperature than the environment temperature of the place to which the user has moved, for a while. For example, JP 2003-156469 A describes that when the measuring instrument is moved from an environment at 40° C. or 10° C. to an environment at 25° C., it takes approximately 30 minutes before the temperature of the measuring instrument is settled at 25° C. In the measurement of the reaction temperature with a temperature sensor of a measuring instrument, it is not easy to completely eliminate the influence of the temperature of the measuring instrument. Therefore, similarly in the biosensor systems described in JP 2001-235444 A, JP 2003-42995 A, and International Publication WO2003/062812, errors tend to occur in the measurement of the analyte concentration when the temperature of the environment where each sensor is used changes rapidly. Furthermore, in the biosensor systems described in JP 2001-235444 A, JP 2003-42995 A, and International Publication WO2003/062812, since the temperature of a blood sample is thermally transferred to the temperature sensor through the resin plate and thermally-conductive member, the reaction temperature that is measured also does not reflect the temperature of the blood sample accurately.

Solution to Problem

The present invention is intended to provide a biosensor system that can prevent a measurement error caused by the temperature of the environment in use from occurring, and a sensor chip suitable for the sensor system. Furthermore, the present invention is intended to provide a measurement method that can improve the accuracy of measuring the analyte concentration in a blood sample.

The present invention provides a biosensor system including a measuring instrument having an operation part, and a sensor chip that is insertable into and removable from the measuring instrument and into which a blood sample is introduced, wherein the sensor chip includes a measurement part A that acquires Data a related to the concentration of an analyte in the blood sample based on the amount of electric current that flows in the blood sample due to a reaction in which an oxidoreductase with the analyte used as a substrate is involved, and a measurement part B that acquires, from the blood sample, Data b for temperature correction of the Data a, and the operation part has a function of determining the concentration of the analyte in the blood sample, with the concentration having been corrected according to the temperature of the blood sample based on the Data a and the Data b.

From another aspect, the present invention provides a sensor chip that is used in the above-mentioned biosensor system and into which a blood sample is introduced, wherein the sensor chip includes a measurement part A that acquires Data a related to the concentration of an analyte in the blood sample based on the amount of electric current that flows in the blood sample due to a reaction in which an oxidoreductase with the analyte used as a substrate is involved, and a measurement part B that acquires, from the blood sample, Data b for temperature correction of the Data a.

From another aspect, the present invention provides a method of measuring the concentration of an analyte in a blood sample. The method includes a step of acquiring Data a related to the concentration of the analyte based on the amount of electric current that flows in the blood sample due to a reaction in which an oxidoreductase with the analyte used as a substrate is involved, a step of acquiring, from the blood sample, Data b for temperature correction of the Data a, and a step of determining the concentration of the analyte in the blood sample, with the concentration having been corrected according to the temperature of the blood sample based on the Data a and the Data b, wherein the step of acquiring the Data b includes a step of applying voltage to a pair of electrodes that have been brought into contact with the blood sample and measuring the amount of electric current that flows in the blood sample according to oxidation or reduction of a redox substance other than the analyte.

Advantageous Effects of Invention

Direct acquisition, from a blood sample, of data for temperature correction of the analyte concentration allows the occurrence of a measurement error caused by the temperature of the environment where the measurement is carried out to be avoided further reliably in the measurement of the analyte concentration in the blood sample. Therefore, the present invention improves the accuracy of measuring the analyte concentration in a blood sample.

BRIEF DESCRIPTION OF DRAWINGS

FIG. 5 is a diagram showing an example of a conversion table.

FIG. 6 is a diagram showing another example of the conversion table.

DESCRIPTION OF EMBODIMENTS

The biosensor system according to the present invention acquires, from a blood sample, data for temperature correction of the analyte concentration with a measurement part disposed in a sensor chip.

Figure 1:
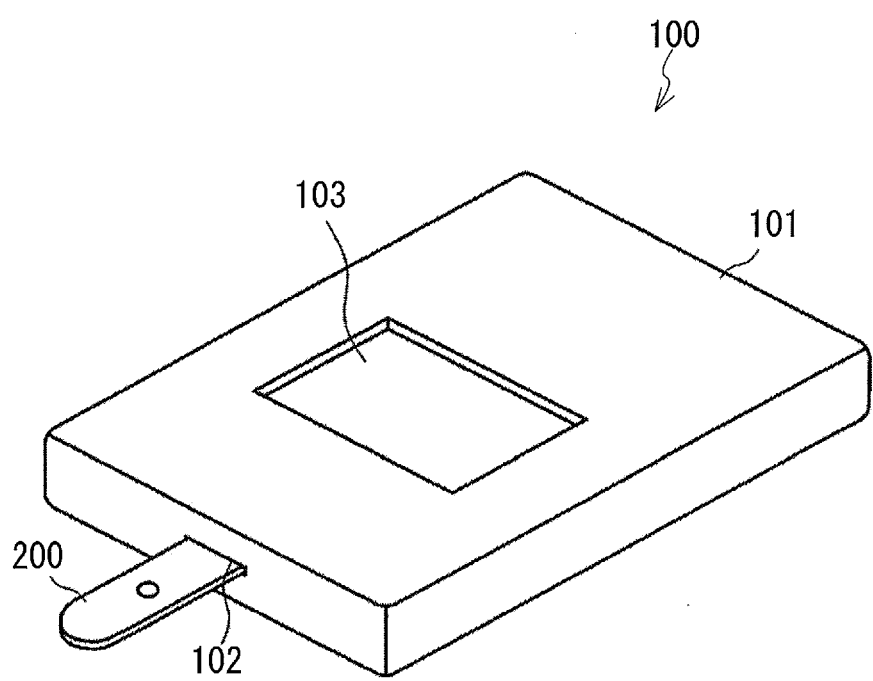
FIG. 1 is a diagram showing an example of the biosensor system according to the present invention.

FIG. 1 is a diagram for explaining an example of the biosensor system according to the present invention. This biosensor system 100 includes a rectangular parallelepiped measuring instrument 101 and a sensor chip 200. A loading port 102 that is a rectangular slit is formed in a side wall of the measuring instrument 101. The sensor chip 200 is loaded removably in the loading port 102 and is connected to the measuring instrument 101. A display part 103 for displaying measurement results is disposed in an approximately central part of one principal surface of the measuring instrument 101.

Figure 2:
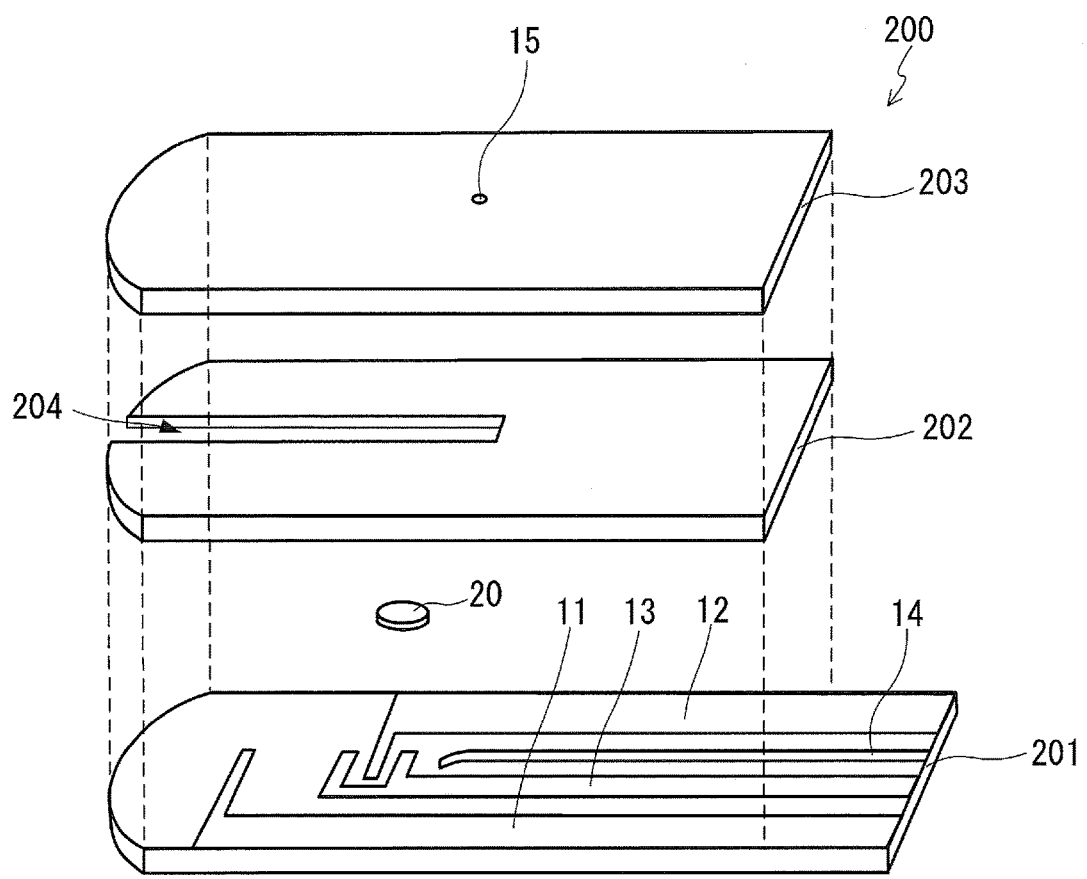
FIG. 2 is an exploded perspective view of an example of the sensor chip according to the present invention.
Figure 3:
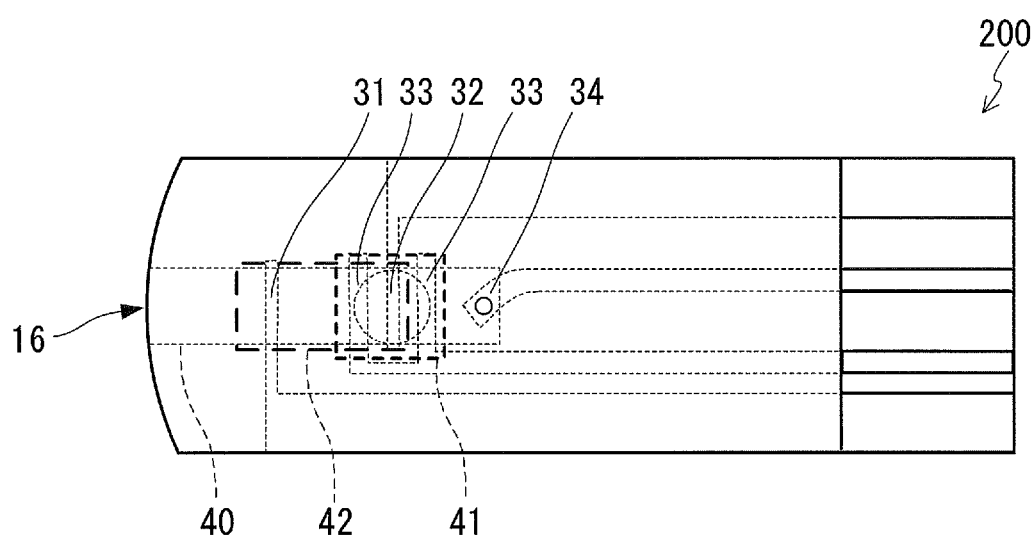
FIG. 3 is a plan view of the example of the sensor chip according to the present invention.

FIG. 2 is an exploded perspective view of the sensor chip 200 and FIG. 3 is a plan view thereof. In this sensor chip 200, a cover 203 is disposed above an insulating substrate 201, with a spacer 202 having a rectangular notched part 204 formed therein being interposed therebetween and with one end part (the right-hand side end in the drawing) of the insulating substrate 201 being left uncovered therewith.

The respective members 201, 202, and 203 are integrated by, for example, bonding or thermal welding. The notched part 204 of the spacer 202 serves as a capillary part 40 that retains a blood sample after the respective members are integrated. The capillary part 40 extends along the long side of the chip 200 to communicate with the outside at one end (the left-hand side end in the drawing) of the spacer 202. In other words, the capillary part 40 communicates with a blood sample feed port 16 that opens to the outside of the chip 200. The cover 203 has an outlet 15 in a part corresponding to the opposite end to the end at which the capillary part 40 communicates with the outside. This allows a blood sample to be drawn easily into the capillary part 40 through the sample feed port 16 by the capillary phenomenon.

On the insulating substrate 201, electrodes 11, 12, 13, and 14 are disposed in such a manner that respective portions (portions 31, 32, 33, and 34) thereof face the capillary part 40. The portion 31 of the electrode 11 is disposed in a position closer to the blood sample feed port 16 as compared to the portion 32 of the electrode 12 and the portions 33 of the electrode 13. The portions 33 of the electrode 13 are parts of the electrode 13 branched in the U-shape and are disposed in positions that allow the portion 32 of the electrode 12 to be interposed therebetween. On the insulating substrate 201, a reaction reagent layer 20 is formed so as to cover the portion 32 of the electrode 12 and the portions 33 of the electrode 13. The reaction reagent layer 20 contains an oxidoreductase with an analyte in a blood sample used as a substrate. The reaction reagent layer 20 is formed in a position away from the portion 31 of the electrode 11.

The sensor chip 200 has a measurement part 41 (a measurement part A) that is composed of an electrode system including the portion 32 of the electrode 12 and the portions 33 of the electrode 13, and the space of part of the capillary part 40 that contains the reaction reagent layer 20 as well as the portion 32 and the portions 33. Furthermore, the sensor chip 200 has a measurement part 42 (a measurement part B) that is composed of an electrode system including the portion 31 of the electrode 11 and the portion 32 of the electrode 12, and the space of part of the capillary part 40 that contains the portion 31 and the portion 32.

As described later, the measurement part A acquires Data a related to the analyte concentration in a blood sample based on the amount of electric current that flows in the blood sample due to a reaction in which an oxidoreductase is involved. On the other hand, as described later, the measurement part B acquires, from a blood sample, Data b for temperature correction of Data a, more specifically, Data b related to the amount of electric current that flows in the blood sample according to oxidation or reduction of a redox substance other than the analyte, which is a reaction in which an oxidoreductase used for acquiring Data a is not involved. In this manner, the measurement part B can be in a state of acquiring Data b by using a member that comes into contact with a blood sample, more specifically, an electrode that comes into contact with a blood sample. In this case, the data related to the amount of electric current denotes the amount of the electric current or the converted value of the amount of the electric current. The redox substance other than the analyte is, for example, at least one selected from ascorbic acid, uric acid, acetaminophen, ferricyanide, p-benzoquinone, a p-benzoquinone derivative, oxidized phenazine methosulfate, methylene blue, ferricinium, and a ferricinium derivative. The redox substance other than the analyte may be a solvent, for example, water in the case of a blood sample.

In the measurement part A, the electrode 12 functions as a working electrode and the electrode 13 functions as a counter electrode. In the measurement part B, the electrode 12 functions as a counter electrode and the electrode 11 functions as a working electrode. The measurement part A and the measurement part B may be in the state of sharing the electrode 12 as shown in the drawing or in the state where each of them has a pair of electrodes. As described above, in the sensor chip 200, the measurement part B has electrodes that apply voltage to a blood sample.

The portion 34 of the electrode 14 is disposed in the vicinity of the end on the back side of the capillary part 40, or in other words, in the vicinity of the opposite end to the end that communicates with the outside. Application of voltage between the electrode 14 and the electrode 11 makes it possible to easily detect the state where a blood sample has been introduced into the back of the capillary part 40. Voltage may be applied between the electrode 14 and the electrode 12 or the electrode 13 instead of the electrode 11.

The electrodes 11, 12, 13, and 14 each are connected to a lead (not shown in the drawings). One end of the lead is exposed outside the chip 200 at the end of the insulating substrate 201 that is not covered with the spacer 202 and the cover 203 so that voltage can be applied between the respective electrodes.

Examples of the analyte in a blood sample includes substances other than hemocyte, for example, glucose, albumin, lactic acid, bilirubin, and cholesterol. The oxidoreductase to be used is one with the target analyte used as a substrate. Examples of the oxidoreductase include glucose oxidase, glucose dehydrogenase, lactate oxidase, lactate dehydrogenase, bilirubin oxidase, and cholesterol oxidase. The amount of oxidoreductase in the reaction reagent layer can be, for example, in the range of 0.01 to 100 units (U), preferably 0.05 to 10 U, and more preferably 0.1 to 5 U.

Desirably, the reaction reagent layer 20 contains an electron mediator having a function of transferring electrons produced by an enzyme reaction to electrodes, such as potassium ferricyanide, p-benzoquinone, a p-benzoquinone derivative, oxidized phenazine methosulfate, methylene blue, ferricinium, and a ferricinium derivative. The reaction reagent layer 20 may contain a water-soluble polymer in order to improve the formability of the reaction reagent layer. The water-soluble polymer can be, for example, at least one selected from carboxymethylcellulose (CMC), hydroxyethylcellulose, hydroxypropylcellulose, methylcellulose, ethylcellulose, ethylhydroxyethylcellulose, carboxyethylcellulose, polyvinyl alcohol, polyvinylpyrrolidone, polyamino acids such as polydin, polystyrene sulfonate, gelatin and derivatives thereof, polyacrylic acid and salt thereof, polymethacrylic acid and salt thereof, starch and derivatives thereof, maleic anhydride polymer and salt thereof, and agarose gel and derivatives thereof.

Examples of the material for the insulating substrate 201, the spacer 202, and the cover 203 include polyethylene terephthalate, polycarbonate, polyimide, polyethylene, polypropylene, polystyrene, polyvinyl chloride, polyoxymethylene, monomer cast nylon, polybutylene terephthalate, resins such as methacrylic resin and ABS resin, and further glass.

The electrodes 11, 12, 13, and 14 can be formed of known conductive materials such as palladium, platinum, gold, silver, titanium, copper, nickel, and carbon.

Figure 4:
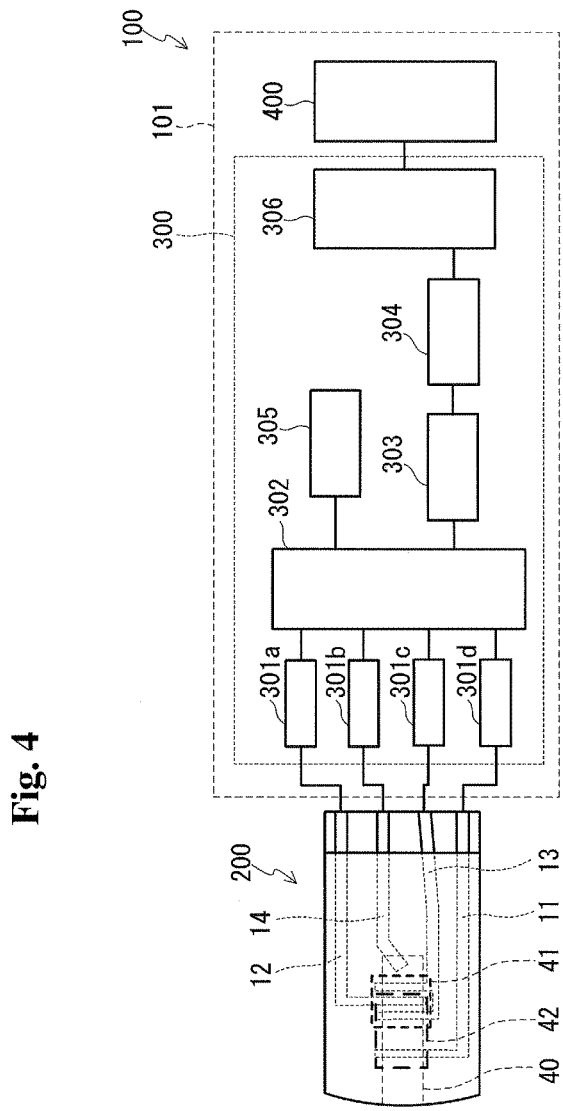
FIG. 4 is a diagram showing an example of the circuit configuration in the biosensor system according to the present invention.

FIG. 4 is a diagram showing an example of the circuit configuration for measuring the analyte concentration in a blood sample in the biosensor system 100. The measuring instrument 101 includes a control circuit 300 for applying voltage between at least two electrodes selected from the electrodes 11, 12, 13, and 14 in the sensor chip 200, and a liquid crystal display (LCD) 400 that corresponds to the display part of the measuring instrument.

The control circuit 300 includes four connectors 301a, 301b, 301c, and 301d, a switching circuit 302, a current-voltage conversion circuit 303, an analog-digital (A-D) conversion circuit 304, a reference voltage source 305, and an operation part 306. The control circuit 300 can switch electric potential to be applied to one electrode through the switching circuit 302 so that the one electrode can be used as a positive electrode or a negative electrode.

The operation part 306 has a known central processing unit (CPU) and a conversion table for determining the analyte concentration in a blood sample based on the above-mentioned Data a and Data b. In a conventional biosensor system, the analyte concentration is corrected with referring to a conversion table in which correction factors provided based on the environmental temperature are described. More specifically, in a conventional biosensor system, after the analyte concentration is calculated provisionally with referring to a conversion table for provisional measurement, the analyte concentration is corrected with referring to a conversion table for temperature correction. The present inventors found that when the temperature of a blood sample varied, the amount of electric current that flowed in a blood sample due to a reaction in which an oxidoreductase was involved could vary in the same manner as the amount of electric current that flowed in the blood sample according to oxidation or reduction of a redox substance other than the analyte, which was a reaction in which the oxidoreductase was not involved. As described later, when the biosensor system is designed suitably, the influence of the temperature of a blood sample in the measurement of the analyte concentration can be eliminated based on a conversion table established using the above-mentioned relationship, without measuring the temperature of, for example, the blood sample.

The operation part 306 is in the state where one conversion table established in this manner is stored but is not in the state where a plurality of conversion tables established per temperature of, for example, a blood sample is stored. FIG. 5 is a diagram showing an example of the conversion table of the operation part 306 and FIG. 6 is a diagram showing another example thereof. As shown in FIG. 5, in the conversion table of the operation part 306, three types of data may be described that include Data c, Data d, and the analyte concentrations in reference blood samples corresponding to Data c and Data d. Data c is related to the amount of electric current that flows in a reference blood sample whose analyte concentration is known and whose temperature is fixed at one value. Data c was acquired from the reference blood sample under the same voltage application condition as that under which the above-mentioned Data a was acquired. Data d is related to the amount of electric current that flows in a reference blood sample. Data d was acquired from the reference blood sample under the same voltage application condition as that under which the above-mentioned Data b was acquired. As described above, each data related to the amount of electric current denotes the amount of the electric current or the converted value of the amount of the electric current. As shown in FIG. 6, in the conversion table of the operation part 306, one converted value based on Data c and Data d may be described instead of Data c and Data d. More specifically, in this conversion table, two types of data may be described that include data obtained by dividing Data c by Data d instead of Data c and Data d, and the analyte concentrations corresponding to Data c and Data d. As described above, the conversion table of the operation part 306 is not in the state where the relationship between the analyte concentration and the temperature of a blood sample or environmental temperature is described. Desirably, the conversion table is prepared for each biosensor system. Preferably, the temperature of each reference blood sample is in the range of higher than 10° C. but lower than 40° C. and further in the range of 17° C. or more to 33° C. or less, as described later.

Measurement of the analyte concentration in a blood sample using the biosensor system 100 is carried out, for example, as follows.

First, according to a command of the CPU of the operation part 306, the electrode 13 is connected to the current-voltage conversion circuit 303 through the connector 301c and the electrode 14 is connected to the reference voltage source 305 through the connector 301b. Thereafter, according to a command of the CPU, a constant voltage is applied between both the electrodes. The voltage is, for example, 0.01 to 2 V, preferably 0.1 to 1 V, and more preferably 0.2 to 0.5 V when the electrode 14 and the electrode 13 are indicated as a positive electrode and a negative electrode, respectively. This voltage is applied between the time when the sensor chip is inserted into the measurement part and the time when the blood sample is introduced into the back of the capillary part 40. When the blood sample is introduced into the capillary part 40 from the blood sample feed port of the sensor chip 200, electric current flows between the electrode 14 and the electrode 13. By identifying the amount of electric current that has increased thereby per unit time, it is detected that the capillary part has been filled with the blood sample. The value of the electric current is converted to a voltage value by the current-voltage conversion circuit 303 and then to a digital value by the A-D conversion circuit 304 to be input to the CPU. Based on the digital value, the CPU detects that the blood sample has been introduced into the back of the capillary part.

After introduction of a blood sample, the analyte in the blood sample and an oxidoreductase are allowed to react with each other in the range of, for example, 0 to 60 seconds, preferably 0 to 30 seconds, and more preferably 0 to 15 seconds.

Subsequently, the above-mentioned Data a is acquired as follows. First, the switching circuit 302 operates according to a command of the CPU and thereby the electrode 12 is connected to the current-voltage conversion circuit 303 through the connector 301a and the electrode 13 is connected to the reference voltage source 305 through the connector 301c. Thereafter, a measurement sequence in the measurement part A is input according to a command of the CPU. In that case, the voltage is, for example, 0.05 to 1 V, preferably 0.1 to 0.8 V, and more preferably 0.2 to 0.6 V when the electrode 12 and the electrode 13 are indicated as a positive electrode and a negative electrode, respectively. The period of voltage application is in the range of 0.1 to 30 seconds, preferably 0.1 to 15 seconds, and more preferably 0.1 to 5 seconds. A signal that indicates acquisition of Data a is provided for the measurement part A from the control circuit, and thereby the amount of electric current that flowed between both the electrodes according to application of the voltage is converted to a voltage value by the current-voltage conversion circuit 303 and then to a digital value by the A-D conversion circuit 304 to be input to the CPU, which is stored as Data a in the memory of the operation part 306. From the viewpoint of accelerating measurement of the analyte concentration, it is preferable that the control circuit provide the measurement part A with a signal that indicates acquisition of Data a within the range of at least 0.5 second but less than 2.5 seconds from the time when the blood sample has been introduced into the capillary part of the sensor chip.

Thereafter, the above-mentioned Data b is acquired as follows. First, the switching circuit 303 operates according to a command of the CPU and thereby the electrode 11 is connected to the current-voltage conversion circuit 303 through the connector 301d and the electrode 12 is connected to the reference voltage source 305 through the connector 301a. Subsequently, according to a command of the CPU, a constant voltage is applied between both the electrodes in the measurement part B. The voltage is, for example, 0.1 to 5 V, preferably 0.2 to 3 V, and more preferably 0.5 to 2.5 V when the electrode 11 and the electrode 12 are indicated as a positive electrode and a negative electrode, respectively. The period of voltage application is in the range of 0.1 to 30 seconds, preferably 0.1 to 10 seconds, and more preferably 0.1 to 5 seconds. A signal that indicates acquisition of Data b is provided for the measurement part B from the control circuit, and thereby the amount of electric current that flowed between both the electrodes according to application of the voltage is converted to a voltage value by the current-voltage conversion circuit 303 and then to a digital value by the A-D conversion circuit 304 to be input to the CPU, which is stored as Data b in the memory of the operation part 306. Data b may be acquired prior to Data a. In that case, with consideration given to generation of a reduced mediator on the counter electrode in acquiring Data b, it is not preferable that the working electrode to be used for acquiring Data a be used as the counter electrode, but it is preferable that the counter electrode to be used for acquiring Data a be used. Furthermore, an independent electrode that is different from the electrode that is used for acquiring Data a may be disposed as a counter electrode. In that case, it is preferable that the oxidized mediator be disposed on the counter electrode. When one electrode is used as the working electrode and the counter electrode in acquiring Data a and Data b, since the redox reaction that occurs at the surface of the electrode may become a rate-limiting step. Therefore, from the viewpoint of avoiding such a problem, it is preferable that Data b be acquired after Data a. Furthermore, when Data b is acquired in such an order, it is possible to further reliably detect the amount of electric current that flows in the blood sample according to oxidation or reduction of a redox substance other than the analyte, which is a reaction in which an oxidoreductase used for acquiring Data a is not involved.

Subsequently, the operation part 306 refers to the conversion table and then determines the analyte concentration in the blood sample based on Data a and Data b. Then, the analyte concentration thus determined is displayed in LCD 400. The operation program for determining it can be designed suitably according to the data structure for the conversion table. When the numerical data that perfectly corresponds to Data a and Data b is not described in the conversion table, the analyte concentration can be determined from the data that is described in the conversion table and that is approximated to Data a and Data b, by using a known linear interpolation method.

The biosensor system according to the present invention can eliminate the influence of the temperature of a blood sample in the measurement of the analyte concentration to such an extent that in a blood sample X with a temperature of 17° C. and a blood sample Y with a temperature of 33° C. having the same components as those of the blood sample X, a numerical value (Z) obtained by dividing the value of Data b by the value of Data a becomes substantially constant. More specifically, a numerical value represented by $Z_x/Z_y$ can be around 1.0, where $Z_x$ and $Z_y$ denote the numerical values obtained from the blood sample X and the blood sample Y, respectively. In the case of measuring the glucose concentration in blood, the analyte concentrations in the blood sample X and the blood sample Y can be in the range of higher than 0 mg/dl but not higher than 1000 mg/dl, for example, in the range of 10 mg/dl to 600 mg/dl.

In order to eliminate the influence of the temperature of the blood sample in the measurement of the analyte concentration to the above-mentioned extent, it is necessary to design the biosensor system suitably. More specifically, various parameters are controlled that include the composition of the reaction reagent layer, the timing of measuring the amount of electric current that flows in the blood sample due to a reaction in which an oxidoreductase is involved, and the size of the capillary part.

For example, when the reaction reagent layer does not contain a water-soluble polymer or the amount of the water-soluble polymer in the reaction reagent layer is less than 0.2 mass %, it is preferable that the measuring instrument have a control circuit that provides the measurement part A with a signal that indicates acquisition of Data a within the range of at least 0.5 second but less than 2.5 seconds from the time when the blood sample has been introduced into the sensor chip. Furthermore, for example, when the amount of the water-soluble polymer in the reaction reagent layer is 0.2 mass % or more, it is preferable that the measuring instrument have a control circuit that provides the measurement part A with a signal that indicates acquisition of Data a after a lapse of at least 2.5 seconds from the time when the blood sample has been introduced into the sensor chip. The reason therefor is not clear at present but the present inventors think as follows. When the reaction reagent layer contains at least 0.2 mass % of water-soluble polymer, the dissolution rate at which the reagent that contributes to a reaction in the reaction reagent layer is eluted in the blood sample is low and the diffusion rate thereof also is low, so that it takes at least 2.5 seconds until the reaction proceeds smoothly. As indicated in the examples to be described later, when the width of the capillary is in the range of 0.8 mm or narrower, it is desirable to employ the design. Furthermore, when the amount of the water-soluble polymer in the reaction reagent layer is at least 0.2 mass %, the upper limit of the content of the water-soluble polymer can be, for example, 2 mass % and the upper limit of the period of time for indicating acquisition of Data a can be, for example, 15 seconds.

Moreover, for example, when the enzyme level in the reaction reagent layer is at least 1.8 U and the width of the capillary part is in the range exceeding 0.8 mm, as indicated in the examples to be described later, it is preferable that the measuring instrument have a control circuit that provides the measurement part A with a signal that indicates acquisition of Data a within the range of 0.5 second or later, further 1.5 seconds or later, and particularly 2.0 seconds or later, from the time when the blood sample has been introduced into the sensor chip. The upper limit of the period of time for the indication can be, for example, 15 seconds.

Furthermore, as indicated in the examples to be described later, for example, when the enzyme level in the reaction reagent layer is the same, it is preferable that the height of the capillary part be low, more specifically the height thereof be in the range of 0.3 mm or lower, further lower than 0.15 mm, and particularly 0.1 mm or lower. The reason therefor is not clear at present but the present inventors think as follows. When the height of the capillary part is too high, the oxidoreductase eluted from the reaction reagent layer tends to diffuse in the direction away from the surfaces of the electrodes, which results in lack of the enzyme that is involved in an enzyme cycling reaction in the vicinity of the surfaces of the electrodes. The lower limit of the height of the capillary part can be, for example, 0.05 mm.

The biosensor system according to the present invention can measure the analyte concentration with high precision even when the temperature of the environment where the sensor is used has changed rapidly. Therefore, it is not necessary to dispose an environmental temperature measurement part such as a thermistor in the measuring instrument. However, this is not intended to eliminate the disposition of the environmental temperature measurement part in the biosensor system according to the present invention.

In other words, in the biosensor system according to the present invention, the measuring instrument further may include an environmental temperature measurement part that measures the temperature of the environment (measurement environment) where the biosensor system is used. Furthermore, in the biosensor system according to the present invention, the operation part further may include a second conversion table in which the above-mentioned Data c and data (Data e) for correcting Data c according to the temperature of the measurement environment are described, in addition to the above-mentioned conversion table (the first conversion table). An excessively high or low temperature of the measurement environment may lower the accuracy of measurement of the analyte concentration that is carried out using the first conversion table. In such a case, the analyte concentration can be corrected by using the second conversion table instead of the first conversion table. The temperature of the measurement environment, for which the second conversion table is used preferably instead, can be, for example, in the range of 10° C. or lower or in the range of 40° C. or higher. The lower limit of the temperature can be, for example, 0° C. and the upper limit of the temperature can be, for example, 50° C. It is sufficient to use the first conversion table when the temperature of the measurement environment is in the range of higher than 10° C. but lower than 40° C.

In the biosensor system according to the present invention, the state is not eliminated where the first conversion table and the second conversion table are stored in one data table, more specifically, where Data c, Data d, and Data e are related to one another and are described in one data table. Such a data table further may contain data (a correction factor) for correcting the analyte concentration, according to the temperature of the measurement environment, that is calculated with referring to the first conversion table when, for example, the temperature of the measurement environment is in the range of 10° C. or lower or in the range of 40° C. or higher.

In the biosensor system according to the present invention, the measuring instrument further may includes a control circuit for providing the environmental temperature measurement part with a signal that indicates implementation of first temperature measurement before acquisition of the above-mentioned Data a and Data b and a signal that indicates implementation of second temperature measurement after acquisition of Data a and Data b. The biosensor system according to the present invention also can be configured so that when the temperatures measured by the first temperature measurement and the second temperature measurement are indicated as a first temperature and a second temperature, respectively, the operation part determines:

i) the analyte concentration in a blood sample based on Data a and Data b with referring to the first conversion table when the first temperature and the second temperature satisfy the following relational expression (1):

$$2.5° C. \leq |(\text{Second Temperature})-(\text{First Temperature})| \quad (1), \text{ and}$$

ii) the analyte concentration in the blood sample based on Data a and data related to the first temperature and/or the second temperature instead of Data b with referring to the second conversion table when the first temperature and the second temperature satisfy the following relational expression (2):

$$|(\text{Second Temperature})-(\text{First Temperature})| < 2.5° C. \quad (2).$$

From the viewpoint of further reliably detecting the change in environmental temperature, it is preferable that the second temperature measurement be carried out after a lapse of at least 5 seconds, preferably at least 15 seconds, and further preferably at least 30 seconds from the first temperature measurement. Thus, the biosensor system of the present invention may include a control circuit that provides the environmental temperature measurement part with a signal that indicates implementation of the second temperature measurement after a lapse of at least 5 seconds, preferably at least 15 seconds, and further preferably at least 30 seconds from the first temperature measurement. For example, the average value of the first temperature and the second temperature can be used as the data related to the first temperature and/or the second temperature. Furthermore, the data may be temperature or may be a converted value of the temperature.

The biosensor system according to the present invention may include a control circuit that provides the environmental temperature measurement part with a signal for measuring environmental temperature at regular intervals after the first temperature measurement and detecting the temperature transition thereof per unit time. This can facilitate judgment of the reliability (presence or absence of failure) of the environmental temperature measurement part such as a thermistor.

As described above, the method of measuring the analyte concentration according to the present invention includes a step of applying voltage to a pair of electrodes that have been brought into contact with the blood sample and measuring the amount of electric current that flows in the blood sample according to oxidation or reduction of a redox substance other than the analyte, and thereby the above-mentioned Data b is acquired. The analyte concentration in a blood sample based on Data a and Data b can be determined with referring to the above-mentioned first conversion table.

The method of measuring the analyte concentration according to the present invention further may include a step of measuring the environmental temperature around the blood sample. The step may include a first temperature measurement step of measuring the environmental temperature before acquisition of Data a and Data b and a second temperature measurement step of measuring the environmental temperature after acquisition of Data a and Data b.

The method of measuring the analyte concentration according to the present invention can be designed so that when the temperatures measured in the first temperature measurement step and the second temperature measurement step are indicated as a first temperature and a second temperature, respectively, i) the analyte concentration in a blood sample is determined based on Data a and Data b with referring to the above-mentioned first conversion table when the first temperature and the second temperature satisfy the following relational expression (1):

$$2.5° C. \leq |(\text{Second Temperature})-(\text{First Temperature})| \quad (1), \text{ and}$$

ii) the analyte concentration in the blood sample is determined based on Data a and data related to the first temperature and/or the second temperature instead of Data b with referring to the above-mentioned second conversion table when the first temperature and the second temperature satisfy the following relational expression (2):

$$|(\text{Second Temperature})-(\text{First Temperature})| < 2.5° C. \quad (2).$$

From the viewpoint of further reliably detecting the change in environmental temperature, it is preferable that the second temperature measurement be carried out after a lapse of at least 5 seconds, preferably at least 15 seconds, and further preferably at least 30 seconds from the first temperature measurement. For example, the average value of the first temperature and the second temperature can be used as the data related to the first temperature and/or the second temperature. Furthermore, the data may be temperature or may be a converted value of the temperature.

EXAMPLES

Hereinafter, the present invention is described in further detail using examples.

Example 1

A sensor chip shown in FIGS. 2 and 3 was produced. The capillary part was designed so as to have a width of 0.6 mm, a length (depth) of 2.5 mm, and a height of 0.1 mm. The reaction reagent layer was formed as follows. A glucose dehydrogenase, potassium ferricyanide (manufactured by Kanto Chemical Co., Inc.), taurine (manufactured by Nacalai Tesque, Inc.), and maltitol (manufactured by Hayashibara Co., Ltd.) were dissolved in a CMC aqueous solution (Cellogen HE-1500F; manufactured by DAI-ICHI KOGYO SEIYAKU Co., Ltd.) and thereby a reagent solution was obtained. The reagent solution was applied onto a polyethylene terephthalate substrate in such a manner that in the reaction reagent layer, the enzyme level was 2.0 U/sensor, the amount of CMC was 0.05 mass %, the amount of potassium ferricyanide was 2.5 mass %, the amount of taurine was 1.5 mass %, and the amount of maltitol was 0.1 mass %. Thereafter, it was dried in an atmosphere with a humidity of 45% and a temperature of 21° C. Each electrode was formed of palladium.

Blood was collected from three subjects. A glucose concentrated solution was added to the respective bloods so that the glucose concentrations thereof became 50 mg/dl, 100 mg/dl, 250 mg/dl, 400 mg/dl, and 600 mg/dl. Thus, blood samples were prepared.

Each blood sample was introduced into the capillary part of the sensor chip. The temperature of the blood sample was set at 17° C., 25° C., or 33° C. Subsequently, a voltage of 0.25 V was applied between the working electrode (the electrode 12) and the counter electrode (the electrode 13) in the measurement part A, and electric current (glucose response) that flowed between the electrodes due to the enzyme cycling reaction in which the above-mentioned enzyme and glucose were involved was measured one second after completion of introduction of the blood sample.

Thereafter, a voltage of 2.5 V was applied between the working electrode (the electrode 11) and the counter electrode (the electrode 12) in the measurement part B, and electric current (response for temperature correction) that flowed between the electrodes was measured three seconds after completion of introduction of the blood sample.

Table 1 indicates the response current values of the glucose response and the response current values of the response for temperature correction. Furthermore, Table 1 also indicates numerical values (Z) obtained by dividing the response current values of the response for temperature correction by the response current values of the glucose response. Table 1 also indicates numerical values ($Z_x/Z_y$) obtained by dividing the above-mentioned numerical values ($Z_x$) obtained from the blood samples with a temperature of 17° C. by the above-mentioned numerical values ($Z_y$) obtained from the blood samples with a temperature of 33° C. Moreover, Table 2 indicates the maximum rate of deviation (the maximum fluctuation width) of the value of $Z_x/Z_y$ from 1.0 as well as the size of the capillary part, the timing at which each response is measured, the enzyme level, and the amount of CMC. Table 2 also indicates those values with respect to the following examples and reference examples.

TABLE 1

| Glucose Response (µA) | | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose Concentration (mg/dl) | 50 | 0.6200 | 0.7400 | 0.8400 | 0.4933 | 0.6000 | 0.6800 | 0.4033 | 0.4833 | 0.5667 |
| | 100 | 0.9900 | 1.1200 | 1.2867 | 0.7633 | 0.8633 | 0.9933 | 0.5700 | 0.6600 | 0.7667 |
| | 250 | 1.9900 | 2.3167 | 2.5567 | 1.4633 | 1.6633 | 1.8600 | 1.0567 | 1.1633 | 1.3433 |
| | 400 | 3.0867 | 3.4533 | 3.9533 | 2.2500 | 2.4800 | 2.7900 | 1.5533 | 1.6833 | 1.9133 |
| | 600 | 4.3933 | 5.0700 | 5.6033 | 3.2100 | 3.5400 | 4.0233 | 2.2933 | 2.4067 | 2.7767 |

| Response for Temperature Correction (µA) | | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose Concentration (mg/dl) | 50 | 49.9000 | 58.6333 | 65.9667 | 36.1333 | 42.9667 | 48.9000 | 22.3000 | 26.4667 | 30.7667 |
| | 100 | 49.7667 | 57.8000 | 65.4667 | 36.0667 | 42.3000 | 48.2333 | 22.5000 | 26.5333 | 30.2333 |
| | 250 | 48.9667 | 58.3000 | 65.1667 | 35.8000 | 42.5667 | 47.4333 | 22.3667 | 26.3667 | 30.3000 |
| | 400 | 49.9333 | 57.7333 | 65.6000 | 36.2667 | 42.0333 | 48.2667 | 22.6667 | 26.3667 | 30.1667 |
| | 600 | 48.8667 | 57.5667 | 65.3000 | 35.6000 | 41.5667 | 47.5000 | 22.2000 | 26.1333 | 30.0000 |

| Z | | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose Concentration (mg/dl) | 50 | 80.48 | 79.23 | 78.53 | 73.25 | 71.61 | 71.91 | 55.29 | 54.76 | 54.29 |
| | 100 | 50.27 | 51.61 | 50.88 | 47.25 | 49.00 | 48.56 | 39.47 | 40.20 | 39.43 |
| | 250 | 24.61 | 25.17 | 25.49 | 24.47 | 25.59 | 25.50 | 21.17 | 22.67 | 22.56 |
| | 400 | 16.18 | 16.72 | 16.59 | 16.12 | 16.95 | 17.30 | 14.59 | 15.66 | 15.77 |
| | 600 | 11.12 | 11.35 | 11.65 | 11.09 | 11.74 | 11.81 | 9.68 | 10.86 | 10.80 |

| Zx/Zy | | Blood Sample A | Blood Sample B | Blood Sample C |
|---|---|---|---|---|
| Glucose Concentration (mg/dl) | 50 | 1.025 | 1.019 | 1.018 |
| | 100 | 0.988 | 0.973 | 1.001 |
| | 250 | 0.965 | 0.959 | 0.938 |
| | 400 | 0.975 | 0.932 | 0.925 |
| | 600 | 0.955 | 0.939 | 0.896 |

TABLE 2

| | Capillary Size (mm; mm; mm) | Measuring Timing (seconds after) Glucose Response | Measuring Timing (seconds after) Response for Temperature Correction | Enzyme Level/ Sensor | CMC (mass %) | Maximum Fluctuation Width of Zx/Zy (%) |
|---|---|---|---|---|---|---|
| Example 1 | 0.6 × 2.5 × 0.1 | 1 | 3 | 2.0U | 0.05 | 10.4 |
| Example 2 | 0.6 × 2.5 × 0.1 | 2.5 | 3 | 2.0U | 0.05 | 14.4 |
| Example 3 | 0.6 × 2.5 × 0.1 | 1 | 3 | 0.5U | 0.05 | 11.6 |
| Example 4 | 0.6 × 2.5 × 0.1 | 1 | 3 | 1.0U | 0.05 | 16.2 |
| Example 5 | 0.6 × 2.5 × 0.1 | 2.5 | 3 | 0.5U | 0.05 | 32.8 |
| Example 6 | 0.6 × 2.5 × 0.1 | 2.5 | 3 | 1.0U | 0.05 | 21.0 |
| Example 7 | 0.6 × 2.5 × 0.1 | 1 | 3 | 1.0U | 0 | 10.7 |
| Example 8 | 0.6 × 2.5 × 0.1 | 1 | 3 | 1.0U | 0.1 | 15.4 |
| Example 9 | 0.6 × 2.5 × 0.1 | 2.5 | 3 | 1.0U | 0.25 | 11.0 |
| Example 10 | 0.6 × 2.5 × 0.1 | 2.5 | 3 | 1.0U | 0.5 | 15.7 |
| Example 11 | 0.6 × 2.5 × 0.1 | 2.5 | 3 | 1.0U | 0 | 27.7 |
| Example 12 | 0.6 × 2.5 × 0.1 | 2.5 | 3 | 1.0U | 0.1 | 18.3 |
| Example 13 | 0.6 × 2.5 × 0.1 | 1.5 | 3 | 1.0U | 0.25 | 18.9 |
| Example 14 | 0.6 × 2.5 × 0.1 | 1 | 3 | 1.0U | 0.5 | 32.2 |
| Example 15 | 1.0 × 3.0 × 0.1 | 1 | 3 | 1.0U | 0.05 | 14.7 |
| Example 16 | 1.0 × 3.0 × 0.1 | 1.5 | 3 | 1.0U | 0.05 | 10.1 |
| Example 17 | 1.0 × 3.0 × 0.1 | 2.5 | 3 | 2.0U | 0.05 | 9.6 |
| Example 18 | 1.0 × 3.0 × 0.1 | 1 | 3 | 2.0U | 0.05 | 16.0 |

TABLE 2-continued

|  | Capillary Size (mm; mm; mm) | Measuring Timing (seconds after) | | Enzyme Level/ Sensor | CMC (mass %) | Maximum Fluctuation Width of Zx/Zy (%) |
|---|---|---|---|---|---|---|
|  |  | Glucose Response | Response for Temperature Correction |  |  |  |
| Example 19 | 1.0 × 3.0 × 0.1 | 1.5 | 3 | 2.0U | 0.05 | 14.0 |
| Example 20 | 1.0 × 3.0 × 0.1 | 1 | 3 | 0.5U | 0.05 | 15.8 |
| Example 21 | 1.0 × 3.0 × 0.1 | 2.5 | 3 | 0.5U | 0.05 | 30.7 |
| Example 22 | 1.0 × 3.0 × 0.1 | 2.5 | 3 | 1.0U | 0.05 | 19.5 |
| Example 23 | 0.6 × 2.5 × 0.15 | 2.5 | 3 | 1.0U | 0.05 | 24.5 |
| Example 24 | 0.6 × 2.5 × 0.15 | 1 | 3 | 1.0U | 0.05 | 20.3 |

As shown in Table 2, the maximum fluctuation width of the value of $Z_x/Z_y$ in Example 1 was in the range of 12% or less.

Example 2

Various electric current responses were measured in the same manner as in Example 1 except that the glucose response was measured 2.5 seconds after completion of introduction of each blood sample into the capillary part. Table 3 indicates the numerical values (Z and $Z_x/Z_y$) obtained from each blood sample.

TABLE 3

| Z | | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 50.92 | 52.35 | 54.52 | 42.34 | 42.82 | 46.72 | 29.60 | 31.26 | 34.57 |
| Concen- | 100 | 33.93 | 35.75 | 36.44 | 29.16 | 31.10 | 33.11 | 23.20 | 24.19 | 26.52 |
| tration | 250 | 17.57 | 18.07 | 18.65 | 16.50 | 17.30 | 17.79 | 13.95 | 14.65 | 15.20 |
| (mg/dl) | 400 | 11.80 | 12.15 | 12.13 | 11.24 | 11.69 | 12.12 | 9.81 | 10.46 | 10.67 |
|  | 600 | 8.19 | 8.27 | 8.52 | 7.85 | 8.16 | 8.38 | 6.97 | 7.25 | 7.48 |

| Zx/Zy | | Blood Sample A | Blood Sample B | Blood Sample C |
|---|---|---|---|---|
| Glucose | 50 | 0.934 | 0.906 | 0.856 |
| Concen- | 100 | 0.931 | 0.881 | 0.875 |
| tration | 250 | 0.942 | 0.927 | 0.918 |
| (mg/dl) | 400 | 0.973 | 0.927 | 0.919 |
|  | 600 | 0.961 | 0.937 | 0.932 |

As shown in Table 2, the maximum fluctuation width of the value of $Z_x/Z_y$ in Example 2 was in the range of 17% or less.

Example 3

Various electric current responses were measured in the same manner as in Example 1 except that a sensor chip with an enzyme level of 0.5 U per sensor was used. Table 4 indicates the numerical values (Z and $Z_x/Z_y$) obtained from each blood sample.

TABLE 4

| Z | | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 49.32 | 52.02 | 51.48 | 45.81 | 48.31 | 47.73 | 32.77 | 36.27 | 37.05 |
| Concen- | 100 | 30.66 | 31.84 | 32.86 | 29.42 | 30.31 | 31.61 | 23.82 | 25.65 | 25.42 |
| tration | 250 | 14.73 | 15.05 | 15.34 | 14.39 | 15.05 | 15.57 | 12.68 | 13.59 | 13.90 |
| (mg/dl) | 400 | 10.22 | 10.27 | 10.10 | 9.95 | 9.99 | 10.66 | 8.65 | 9.15 | 9.36 |
|  | 600 | 7.97 | 7.31 | 7.24 | 7.49 | 7.17 | 7.26 | 6.14 | 6.37 | 6.65 |

TABLE 4-continued

| Zx/Zy | | Blood Sample A | Blood Sample B | Blood Sample C |
|---|---|---|---|---|
| Glucose | 50 | 0.958 | 0.960 | 0.884 |
| Concen- | 100 | 0.933 | 0.931 | 0.937 |
| tration | 250 | 0.960 | 0.924 | 0.912 |
| (mg/dl) | 400 | 1.012 | 0.933 | 0.924 |
|  | 600 | 1.101 | 1.032 | 0.923 |

As shown in Table 2, the maximum fluctuation width of the value of $Z_x/Z_y$ in Example 3 was in the range of 12% or less.

Example 4

Various electric current responses were measured in the same manner as in Example 1 except that a sensor chip with an enzyme level of 1.0 U per sensor was used. Table 5 indicates the numerical values (Z and $Z_x/Z_y$) obtained from each blood sample.

TABLE 5

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 47.43 | 48.48 | 51.88 | 38.14 | 40.88 | 45.36 | 27.20 | 29.01 | 31.72 |
| Concen- | 100 | 30.14 | 31.34 | 33.75 | 26.74 | 27.83 | 30.09 | 19.97 | 22.88 | 23.83 |
| tration | 250 | 14.42 | 14.92 | 16.00 | 13.87 | 14.81 | 15.25 | 11.19 | 12.38 | 13.36 |
| (mg/dl) | 400 | 9.89 | 10.14 | 10.49 | 9.32 | 9.65 | 10.51 | 8.22 | 8.48 | 9.21 |
|  | 600 | 7.19 | 7.09 | 7.26 | 6.45 | 6.55 | 7.17 | 5.60 | 6.07 | 6.48 |

| Zx/Zy | | Blood Sample A | Blood Sample B | Blood Sample C |
|---|---|---|---|---|
| Glucose | 50 | 0.914 | 0.841 | 0.858 |
| Concen- | 100 | 0.893 | 0.889 | 0.838 |
| tration | 250 | 0.901 | 0.910 | 0.838 |
| (mg/dl) | 400 | 0.943 | 0.887 | 0.893 |
|  | 600 | 0.990 | 0.900 | 0.864 |

As shown in Table 2, the maximum fluctuation width of the value of $Z_x/Z_y$ in Example 4 was in the range of 17% or less.

Example 5

Various electric current responses were measured in the same manner as in Example 3 except that the glucose response was measured 2.5 seconds after completion of introduction of each blood sample into the capillary part. Table 6 indicates the numerical values (Z and $Z_x/Z_y$) obtained from each blood sample.

TABLE 6

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 75.73 | 72.85 | 67.61 | 73.66 | 66.78 | 58.36 | 56.75 | 51.33 | 42.72 |
| Concen- | 100 | 45.73 | 44.57 | 42.92 | 46.69 | 41.95 | 39.32 | 39.35 | 35.92 | 29.71 |
| tration | 250 | 20.97 | 20.92 | 20.44 | 22.02 | 21.54 | 20.45 | 20.23 | 19.65 | 17.58 |
| (mg/dl) | 400 | 13.76 | 13.85 | 13.50 | 14.55 | 14.06 | 14.16 | 13.62 | 13.23 | 12.42 |
|  | 600 | 10.33 | 9.49 | 9.39 | 10.33 | 9.88 | 9.73 | 9.43 | 9.34 | 8.92 |

TABLE 6-continued

|  | Zx/Zy | Blood Sample A | Blood Sample B | Blood Sample C |
| --- | --- | --- | --- | --- |
| Glucose | 50 | 1.120 | 1.262 | 1.328 |
| Concen- | 100 | 1.065 | 1.187 | 1.324 |
| tration | 250 | 1.026 | 1.077 | 1.151 |
| (mg/dl) | 400 | 1.019 | 1.028 | 1.097 |
|  | 600 | 1.100 | 1.062 | 1.057 |

As shown in Table 2, the maximum fluctuation width of the value of $Z_x/Z_y$ in Example 5 was in the range exceeding 17%.

Example 6

Various electric current responses were measured in the same manner as in Example 4 except that the glucose response was measured 2.5 seconds after completion of introduction of each blood sample into the capillary part. Table 7 indicates the numerical values (Z and $Z_x/Z_y$) obtained from each blood sample.

TABLE 7

|  |  | Blood Sample A | | | Blood Sample B | | | Blood Sample C | | |
| --- | --- | --- | --- | --- | --- | --- | --- | --- | --- | --- |
| Z |  | 17° C. | 25° C. | 33° C. | 17° C. | 25° C. | 33° C. | 17° C. | 25° C. | 33° C. |
| Glucose | 50 | 75.75 | 73.19 | 71.31 | 69.33 | 66.95 | 62.88 | 52.79 | 48.98 | 43.62 |
| Concen- | 100 | 47.02 | 46.39 | 45.70 | 45.94 | 43.62 | 41.72 | 37.18 | 35.82 | 31.68 |
| tration | 250 | 21.52 | 21.58 | 22.02 | 22.32 | 22.26 | 21.39 | 19.45 | 19.57 | 18.47 |
| (mg/dl) | 400 | 14.31 | 14.46 | 14.59 | 14.64 | 14.64 | 14.93 | 13.49 | 13.44 | 13.14 |
|  | 600 | 10.08 | 9.87 | 10.05 | 9.97 | 9.87 | 10.20 | 9.16 | 9.31 | 9.37 |

|  | Zx/Zy | Blood Sample A | Blood Sample B | Blood Sample C |
| --- | --- | --- | --- | --- |
| Glucose | 50 | 1.062 | 1.103 | 1.210 |
| Concen- | 100 | 1.029 | 1.101 | 1.174 |
| tration | 250 | 0.977 | 1.043 | 1.053 |
| (mg/dl) | 400 | 0.981 | 0.981 | 1.027 |
|  | 600 | 1.003 | 0.977 | 0.978 |

As shown in Table 2, the maximum fluctuation width of the value of $Z_x/Z_y$ in Example 6 was in the range exceeding 17%.

Example 7

Various electric current responses were measured in the same manner as in Example 4 except that a sensor chip in which the reaction reagent layer did not contain CMC was used. Table 8 indicates the numerical values (Z and $Z_x/Z_y$) obtained from each blood sample.

TABLE 8

|  |  | Blood Sample A | | | Blood Sample B | | | Blood Sample C | | |
| --- | --- | --- | --- | --- | --- | --- | --- | --- | --- | --- |
| Z |  | 17° C. | 25° C. | 33° C. | 17° C. | 25° C. | 33° C. | 17° C. | 25° C. | 33° C. |
| Glucose | 50 | 44.06 | 45.35 | 46.19 | 34.85 | 39.31 | 39.02 | 24.69 | 27.86 | 27.42 |
| Concen- | 100 | 29.41 | 30.32 | 31.51 | 24.66 | 26.79 | 26.78 | 20.02 | 20.25 | 21.44 |
| tration | 250 | 14.09 | 14.89 | 14.88 | 13.16 | 13.62 | 14.04 | 11.23 | 11.52 | 12.02 |
| (mg/dl) | 400 | 9.45 | 9.95 | 10.27 | 8.91 | 9.55 | 9.62 | 8.01 | 7.88 | 8.39 |
|  | 600 | 6.87 | 6.93 | 7.05 | 6.32 | 6.62 | 6.66 | 5.48 | 5.72 | 5.69 |

TABLE 8-continued

|  | Zx/Zy | Blood Sample A | Blood Sample B | Blood Sample C |
|---|---|---|---|---|
| Glucose | 50 | 0.954 | 0.893 | 0.900 |
| Concen- | 100 | 0.933 | 0.921 | 0.934 |
| tration | 250 | 0.947 | 0.937 | 0.934 |
| (mg/dl) | 400 | 0.920 | 0.926 | 0.955 |
|  | 600 | 0.974 | 0.949 | 0.963 |

As shown in Table 2, the maximum fluctuation width of the value of $Z_x/Z_y$ in Example 7 was in the range of 12% or less.

Example 8

Various electric current responses were measured in the same manner as in Example 4 except that a sensor chip in which the amount of CMC in the reaction reagent layer was 0.1 mass % was used. Table 9 indicates the numerical values (Z and $Z_x/Z_y$) obtained from each blood sample.

TABLE 9

| Z |  | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 42.16 | 44.15 | 46.64 | 37.43 | 37.50 | 38.67 | 23.21 | 27.21 | 27.00 |
| Concen- | 100 | 28.56 | 29.95 | 30.65 | 25.05 | 27.29 | 28.63 | 18.63 | 20.20 | 19.78 |
| tration | 250 | 14.24 | 15.44 | 15.51 | 13.31 | 14.03 | 14.50 | 10.69 | 10.67 | 11.84 |
| (mg/dl) | 400 | 9.40 | 9.88 | 10.33 | 8.90 | 9.90 | 9.95 | 7.26 | 7.83 | 8.58 |
|  | 600 | 6.86 | 6.95 | 7.07 | 6.45 | 6.84 | 7.14 | 5.46 | 5.89 | 6.17 |

|  | Zx/Zy | Blood Sample A | Blood Sample B | Blood Sample C |
|---|---|---|---|---|
| Glucose | 50 | 0.904 | 0.968 | 0.860 |
| Concen- | 100 | 0.932 | 0.875 | 0.942 |
| tration | 250 | 0.918 | 0.918 | 0.903 |
| (mg/dl) | 400 | 0.910 | 0.894 | 0.846 |
|  | 600 | 0.970 | 0.903 | 0.885 |

As shown in Table 2, the maximum fluctuation width of the value of $Z_x/Z_y$ in Example 8 was in the range of 17% or less.

Example 9

Various electric current responses were measured in the same manner as in Example 6 except that a sensor chip in which the amount of CMC in the reaction reagent layer was 0.25 mass % was used. Table 10 indicates the numerical values (Z and $Z_x/Z_y$) obtained from each blood sample.

TABLE 10

| Z |  | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 65.23 | 67.30 | 64.14 | 53.86 | 56.44 | 52.78 | 34.19 | 38.39 | 36.38 |
| Concen- | 100 | 43.31 | 44.20 | 44.12 | 37.90 | 39.51 | 38.27 | 27.38 | 29.36 | 27.31 |
| tration | 250 | 21.66 | 21.83 | 21.89 | 19.83 | 20.76 | 20.78 | 15.66 | 16.92 | 17.33 |
| (mg/dl) | 400 | 14.48 | 14.71 | 15.05 | 13.25 | 14.13 | 14.26 | 11.21 | 12.08 | 12.35 |
|  | 600 | 9.99 | 10.28 | 10.19 | 9.29 | 9.97 | 10.03 | 7.75 | 8.45 | 8.71 |

TABLE 10-continued

|  | Zx/Zy | Blood Sample A | Blood Sample B | Blood Sample C |
|---|---|---|---|---|
| Glucose | 50 | 1.017 | 1.020 | 0.940 |
| Concen- | 100 | 0.982 | 0.990 | 1.003 |
| tration | 250 | 0.989 | 0.954 | 0.904 |
| (mg/dl) | 400 | 0.962 | 0.929 | 0.908 |
|  | 600 | 0.980 | 0.926 | 0.890 |

As shown in Table 2, the maximum fluctuation width of the value of $Z_x/Z_y$ in Example 9 was in the range of 12% or less.

Example 10

Various electric current responses were measured in the same manner as in Example 6 except that a sensor chip in which the amount of CMC in the reaction reagent layer was 0.5 mass % was used. Table 11 indicates the numerical values (Z and $Z_x/Z_y$) obtained from each blood sample.

TABLE 11

|  | Z | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 64.29 | 63.57 | 62.14 | 48.00 | 51.96 | 47.64 | 28.62 | 33.82 | 33.20 |
| Concentration | 100 | 43.52 | 43.98 | 45.46 | 36.22 | 37.72 | 34.57 | 24.22 | 25.80 | 24.29 |
| (mg/dl) | 250 | 22.13 | 22.73 | 22.33 | 19.69 | 20.27 | 20.73 | 14.34 | 15.17 | 15.65 |
|  | 400 | 14.79 | 15.17 | 15.22 | 13.11 | 13.87 | 14.09 | 9.95 | 10.85 | 11.81 |
|  | 600 | 10.33 | 10.45 | 10.66 | 9.15 | 9.91 | 10.56 | 7.69 | 8.07 | 8.25 |

|  | Zx/Zy | Blood Sample A | Blood Sample B | Blood Sample C |
|---|---|---|---|---|
| Glucose | 50 | 1.035 | 1.008 | 0.862 |
| Concentration | 100 | 0.957 | 1.048 | 0.997 |
| (mg/dl) | 250 | 0.991 | 0.950 | 0.916 |
|  | 400 | 0.972 | 0.930 | 0.843 |
|  | 600 | 0.969 | 0.866 | 0.932 |

As shown in Table 2, the maximum fluctuation width of the value of $Z_x/Z_y$ in Example 10 was in the range of 17% or less.

Example 11

Various electric current responses were measured in the same manner as in Example 7 except that the glucose response was measured 2.5 seconds after completion of introduction of each blood sample into the capillary part. Table 12 indicates the numerical values (Z and $Z_x/Z_y$) obtained from each blood sample.

TABLE 12

|  | Z | Blood Sample A | | | Blood Sample B | | | Blood Sample C | | |
|---|---|---|---|---|---|---|---|---|---|---|
|  |  | 17° C. | 25° C. | 33° C. | 17° C. | 25° C. | 33° C. | 17° C. | 25° C. | 33° C. |
| Glucose | 50 | 70.79 | 68.88 | 64.52 | 62.05 | 60.22 | 52.90 | 44.50 | 41.87 | 34.84 |
| Concentration | 100 | 45.09 | 44.57 | 42.59 | 41.27 | 40.61 | 35.53 | 33.19 | 30.04 | 26.02 |
| (mg/dl) | 250 | 21.02 | 21.38 | 20.64 | 20.60 | 20.36 | 19.41 | 17.94 | 16.98 | 15.71 |
|  | 400 | 13.77 | 14.16 | 14.21 | 13.59 | 13.84 | 13.48 | 12.20 | 11.73 | 11.50 |
|  | 600 | 9.68 | 9.70 | 9.73 | 9.59 | 9.63 | 9.42 | 8.37 | 8.37 | 7.88 |

TABLE 12-continued

| | Zx/Zy | Blood Sample A | Blood Sample B | Blood Sample C |
|---|---|---|---|---|
| Glucose Concentration (mg/dl) | 50 | 1.097 | 1.173 | 1.277 |
| | 100 | 1.059 | 1.162 | 1.276 |
| | 250 | 1.018 | 1.061 | 1.142 |
| | 400 | 0.969 | 1.008 | 1.061 |
| | 600 | 0.995 | 1.018 | 1.062 |

As shown in Table 2, the maximum fluctuation width of the value of $Z_x/Z_y$ in Example 11 was in the range exceeding 17%.

Example 12

Various electric current responses were measured in the same manner as in Example 8 except that the glucose response was measured 2.5 seconds after completion of introduction of each blood sample into the capillary part. Table 13 indicates the numerical values (Z and $Z_x/Z_y$) obtained from each blood sample.

TABLE 13

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 71.21 | 68.39 | 66.78 | 67.76 | 63.97 | 57.75 | 47.20 | 46.22 | 40.19 |
| Concentration | 100 | 45.22 | 44.75 | 42.80 | 44.26 | 43.45 | 40.39 | 34.83 | 32.95 | 29.44 |
| (mg/dl) | 250 | 21.37 | 22.21 | 21.43 | 21.83 | 21.95 | 21.13 | 18.66 | 18.17 | 17.82 |
| | 400 | 13.85 | 14.15 | 14.44 | 14.29 | 14.87 | 14.40 | 12.51 | 12.84 | 13.13 |
| | 600 | 9.79 | 9.84 | 9.80 | 10.10 | 10.28 | 10.29 | 8.84 | 9.25 | 9.15 |

| | Zx/Zy | Blood Sample A | Blood Sample B | Blood Sample C |
|---|---|---|---|---|
| Glucose Concentration (mg/dl) | 50 | 1.066 | 1.173 | 1.174 |
| | 100 | 1.057 | 1.096 | 1.183 |
| | 250 | 0.997 | 1.033 | 1.047 |
| | 400 | 0.959 | 0.992 | 0.953 |
| | 600 | 0.999 | 0.982 | 0.966 |

As shown in Table 2, the maximum fluctuation width of the value of $Z_x/Z_y$ in Example 12 was in the range exceeding 17%.

Example 13

Various electric current responses were measured in the same manner as in Example 9 except that the glucose response was measured 1.5 seconds after completion of introduction of each blood sample into the capillary part. Table 14 indicates the numerical values (Z and $Z_x/Z_y$) obtained from each blood sample.

TABLE 14

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 47.43 | 51.90 | 52.10 | 36.35 | 40.87 | 40.49 | 21.58 | 26.02 | 26.61 |
| Concentration | 100 | 32.96 | 34.97 | 36.61 | 26.83 | 29.35 | 30.34 | 18.17 | 20.68 | 20.85 |
| (mg/dl) | 250 | 17.31 | 17.77 | 18.25 | 15.04 | 16.16 | 16.84 | 11.26 | 12.46 | 13.73 |
| | 400 | 11.72 | 12.07 | 12.60 | 10.25 | 11.16 | 11.54 | 8.40 | 8.99 | 9.50 |
| | 600 | 8.17 | 8.53 | 8.52 | 7.30 | 7.99 | 8.14 | 5.89 | 6.39 | 6.74 |

TABLE 14-continued

| Zx/Zy | | Blood Sample A | Blood Sample B | Blood Sample C |
|---|---|---|---|---|
| Glucose Concentration (mg/dl) | 50 | 0.910 | 0.898 | 0.811 |
| | 100 | 0.900 | 0.884 | 0.871 |
| | 250 | 0.948 | 0.893 | 0.820 |
| | 400 | 0.930 | 0.888 | 0.884 |
| | 600 | 0.959 | 0.897 | 0.874 |

As shown in Table 2, the maximum fluctuation width of the value of $Z_x/Z_y$ in Example 13 was in the range exceeding 17%.

Example 14

Various electric current responses were measured in the same manner as in Example 10 except that the glucose response was measured 1.0 second after completion of introduction of each blood sample into the capillary part. Table 15 indicates the numerical values (Z and $Z_x/Z_y$) obtained from each blood sample.

TABLE 15

| Z | | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose Concentration (mg/dl) | 50 | 36.89 | 37.26 | 38.20 | 27.05 | 28.86 | 27.29 | 20.90 | 18.78 | 18.57 |
| | 100 | 27.56 | 28.57 | 30.74 | 22.38 | 23.43 | 20.78 | 17.64 | 15.69 | 14.47 |
| | 250 | 16.42 | 16.63 | 16.33 | 14.66 | 14.33 | 14.77 | 13.41 | 10.37 | 10.38 |
| | 400 | 11.45 | 11.62 | 11.47 | 11.55 | 10.40 | 10.22 | 10.95 | 7.77 | 8.28 |
| | 600 | 8.28 | 8.17 | 8.30 | 8.15 | 7.59 | 8.04 | 7.53 | 6.20 | 5.94 |

| Zx/Zy | | Blood Sample A | Blood Sample B | Blood Sample C |
|---|---|---|---|---|
| Glucose Concentration (mg/dl) | 50 | 0.966 | 0.991 | 1.125 |
| | 100 | 0.897 | 1.077 | 1.219 |
| | 250 | 1.006 | 0.993 | 1.292 |
| | 400 | 0.998 | 1.130 | 1.322 |
| | 600 | 0.998 | 1.014 | 1.268 |

As shown in Table 2, the maximum fluctuation width of the value of $Z_x/Z_y$ in Example 14 was in the range exceeding 17%.

Example 15

Various electric current responses were measured in the same manner as in Example 4 except that a sensor chip in which the capillary part had a width of 1.0 mm and a length of 3.0 mm was used. Table 16 indicates the numerical values (Z and $Z_x/Z_y$) obtained from each blood sample.

TABLE 16

| Z | | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose Concentration (mg/dl) | 50 | 24.86 | 25.69 | 26.58 | 20.92 | 23.37 | 24.52 | 15.29 | 17.46 | 17.81 |
| | 100 | 16.05 | 16.73 | 17.10 | 14.74 | 15.80 | 16.32 | 11.62 | 12.93 | 13.11 |
| | 250 | 7.85 | 8.12 | 8.21 | 7.21 | 8.02 | 8.37 | 6.38 | 7.06 | 7.38 |
| | 400 | 5.40 | 5.56 | 5.44 | 5.02 | 5.43 | 5.59 | 4.50 | 4.88 | 5.11 |
| | 600 | 4.21 | 4.03 | 3.86 | 3.71 | 3.88 | 3.93 | 3.21 | 3.46 | 3.59 |

TABLE 16-continued

| | Zx/Zy | Blood Sample A | Blood Sample B | Blood Sample C |
|---|---|---|---|---|
| Glucose Concentration (mg/dl) | 50 | 0.935 | 0.853 | 0.859 |
| | 100 | 0.939 | 0.903 | 0.886 |
| | 250 | 0.956 | 0.861 | 0.864 |
| | 400 | 0.993 | 0.898 | 0.881 |
| | 600 | 1.091 | 0.944 | 0.894 |

As shown in Table 2, the maximum fluctuation width of the value of $Z_x/Z_y$ in Example 15 was in the range of 17% or less.

Example 16

Various electric current responses were measured in the same manner as in Example 15 except that the glucose response was measured 1.5 seconds after completion of introduction of each blood sample into the capillary part. Table 17 indicates the numerical values (Z and $Z_x/Z_y$) obtained from each blood sample.

TABLE 17

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 31.93 | 32.72 | 32.72 | 28.87 | 30.85 | 30.83 | 21.81 | 23.79 | 23.13 |
| Concentration | 100 | 20.00 | 20.62 | 20.75 | 19.37 | 20.31 | 20.28 | 15.85 | 16.91 | 16.54 |
| (mg/dl) | 250 | 9.47 | 9.77 | 9.80 | 9.16 | 10.00 | 10.19 | 8.32 | 8.98 | 9.16 |
| | 400 | 6.41 | 6.53 | 6.45 | 6.28 | 6.66 | 6.81 | 5.74 | 6.13 | 6.32 |
| | 600 | 4.88 | 4.66 | 4.54 | 4.57 | 4.70 | 4.73 | 4.04 | 4.30 | 4.43 |

| | Zx/Zy | Blood Sample A | Blood Sample B | Blood Sample C |
|---|---|---|---|---|
| Glucose Concentration (mg/dl) | 50 | 0.976 | 0.936 | 0.943 |
| | 100 | 0.964 | 0.955 | 0.958 |
| | 250 | 0.966 | 0.899 | 0.908 |
| | 400 | 0.994 | 0.922 | 0.908 |
| | 600 | 1.075 | 0.966 | 0.912 |

As shown in Table 2, the maximum fluctuation width of the value of $Z_x/Z_y$ in Example 16 was in the range of 12% or less.

Example 17

Various electric current responses were measured in the same manner as in Example 2 except that a sensor chip in which the capillary part had a width of 1.0 mm and a length of 3.0 mm was used. Table 18 indicates the numerical values (Z and $Z_x/Z_y$) obtained from each blood sample.

TABLE 18

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 40.33 | 40.15 | 37.68 | 37.27 | 38.34 | 35.99 | 26.65 | 28.01 | 25.00 |
| Concentration | 100 | 25.75 | 25.84 | 24.98 | 25.45 | 25.48 | 24.61 | 20.14 | 19.93 | 18.46 |
| (mg/dl) | 250 | 12.09 | 12.29 | 12.15 | 13.15 | 12.67 | 12.62 | 10.97 | 10.88 | 10.61 |
| | 400 | 7.76 | 7.99 | 8.10 | 8.39 | 8.62 | 8.59 | 7.36 | 7.68 | 7.55 |
| | 600 | 5.58 | 5.57 | 5.59 | 5.75 | 5.90 | 5.91 | 4.91 | 5.40 | 5.43 |

TABLE 18-continued

| | $Z_x/Z_y$ | Blood Sample A | Blood Sample B | Blood Sample C |
|---|---|---|---|---|
| Glucose | 50 | 1.070 | 1.036 | 1.066 |
| Concentration | 100 | 1.031 | 1.034 | 1.091 |
| (mg/dl) | 250 | 0.995 | 1.042 | 1.034 |
| | 400 | 0.958 | 0.977 | 0.975 |
| | 600 | 0.998 | 0.973 | 0.904 |

As shown in Table 2, the maximum fluctuation width of the value of $Z_x/Z_y$ in Example 17 was in the range of 12% or less.

Example 18

Various electric current responses were measured in the same manner as in Example 1 except that a sensor chip in which the capillary part had a width of 1.0 mm and a length of 3.0 mm was used. Table 19 indicates the numerical values (Z and $Z_x/Z_y$) obtained from each blood sample.

TABLE 19

| | Z | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose | 50 | 23.88 | 25.00 | 24.37 | 19.30 | 22.51 | 22.98 | 13.18 | 16.01 | 15.14 |
| Concentration | 100 | 16.48 | 17.33 | 17.03 | 14.62 | 16.17 | 16.91 | 10.94 | 11.56 | 12.02 |
| (mg/dl) | 250 | 8.18 | 8.39 | 8.58 | 8.44 | 8.05 | 8.56 | 6.70 | 6.69 | 7.03 |
| | 400 | 5.36 | 5.52 | 5.70 | 5.50 | 5.74 | 5.91 | 4.62 | 4.92 | 4.90 |
| | 600 | 4.01 | 3.89 | 4.00 | 3.84 | 3.94 | 3.91 | 3.10 | 3.49 | 3.51 |

| | $Z_x/Z_y$ | Blood Sample A | Blood Sample B | Blood Sample C |
|---|---|---|---|---|
| Glucose | 50 | 0.980 | 0.840 | 0.871 |
| Concentration | 100 | 0.968 | 0.865 | 0.910 |
| (mg/dl) | 250 | 0.953 | 0.986 | 0.953 |
| | 400 | 0.940 | 0.931 | 0.943 |
| | 600 | 1.003 | 0.982 | 0.883 |

As shown in Table 2, the maximum fluctuation width of the value of $Z_x/Z_y$ in Example 18 was in the range of 17% or less.

Example 19

Various electric current responses were measured in the same manner as in Example 18 except that the glucose response was measured 1.5 seconds after completion of introduction of each blood sample into the capillary part. Table 20 indicates the numerical values (Z and $Z_x/Z_y$) obtained from each blood sample.

TABLE 20

| | Z | Blood Sample A | | | Blood Sample B | | | Blood Sample C | | |
|---|---|---|---|---|---|---|---|---|---|---|
| | | 17° C. | 25° C. | 33° C. | 17° C. | 25° C. | 33° C. | 17° C. | 25° C. | 33° C. |
| Glucose | 50 | 30.41 | 31.60 | 30.66 | 25.85 | 29.43 | 29.53 | 17.87 | 21.20 | 20.02 |
| Concentration | 100 | 20.12 | 20.96 | 20.71 | 18.68 | 20.19 | 20.79 | 14.27 | 15.05 | 15.28 |
| (mg/dl) | 250 | 9.66 | 9.95 | 10.12 | 10.21 | 9.89 | 10.38 | 8.28 | 8.33 | 8.68 |
| | 400 | 6.26 | 6.49 | 6.68 | 6.56 | 6.89 | 7.05 | 5.57 | 6.01 | 6.01 |
| | 600 | 4.61 | 4.54 | 4.65 | 4.53 | 4.69 | 4.72 | 3.69 | 4.20 | 4.29 |

TABLE 20-continued

| | Zx/Zy | Blood Sample A | Blood Sample B | Blood Sample C |
|---|---|---|---|---|
| Glucose Concentration (mg/dl) | 50 | 0.992 | 0.875 | 0.893 |
| | 100 | 0.972 | 0.899 | 0.934 |
| | 250 | 0.955 | 0.984 | 0.954 |
| | 400 | 0.937 | 0.930 | 0.927 |
| | 600 | 0.991 | 0.960 | 0.860 |

As shown in Table 2, the maximum fluctuation width of the value of $Z_x/Z_y$ in Example 19 was in the range of 17% or less.

Example 20

Various electric current responses were measured in the same manner as in Example 3 except that a sensor chip in which the capillary part had a width of 1.0 mm and a length of 3.0 mm was used. Table 21 indicates the numerical values (Z and $Z_x/Z_y$) obtained from each blood sample.

TABLE 21

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose Concentration (mg/dl) | 50 | 27.18 | 28.97 | 28.06 | 23.73 | 26.25 | 26.79 | 18.32 | 20.12 | 20.96 |
| | 100 | 16.92 | 17.86 | 17.90 | 16.20 | 17.01 | 17.76 | 13.10 | 14.08 | 14.55 |
| | 250 | 8.47 | 8.21 | 8.38 | 7.85 | 8.32 | 8.66 | 6.80 | 7.29 | 7.59 |
| | 400 | 6.24 | 5.98 | 5.68 | 5.75 | 5.77 | 5.73 | 4.73 | 4.92 | 5.25 |
| | 600 | 4.99 | 4.61 | 4.31 | 4.34 | 4.18 | 4.10 | 3.53 | 3.70 | 3.84 |

| | Zx/Zy | Blood Sample A | Blood Sample B | Blood Sample C |
|---|---|---|---|---|
| Glucose Concentration (mg/dl) | 50 | 0.969 | 0.886 | 0.874 |
| | 100 | 0.945 | 0.912 | 0.900 |
| | 250 | 1.011 | 0.906 | 0.896 |
| | 400 | 1.099 | 1.003 | 0.901 |
| | 600 | 1.158 | 1.059 | 0.919 |

As shown in Table 2, the maximum fluctuation width of the value of $Z_x/Z_y$ in Example 20 was in the range of 17% or less.

Example 21

Various electric current responses were measured in the same manner as in Example 5 except that a sensor chip in which the capillary part had a width of 1.0 mm and a length of 3.0 mm was used. Table 22 indicates the numerical values (Z and $Z_x/Z_y$) obtained from each blood sample.

TABLE 22

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose Concentration (mg/dl) | 50 | 43.60 | 42.65 | 38.91 | 43.02 | 41.11 | 36.57 | 35.63 | 32.52 | 27.27 |
| | 100 | 26.37 | 26.07 | 24.66 | 27.33 | 26.22 | 23.94 | 23.94 | 22.33 | 19.31 |
| | 250 | 12.20 | 11.89 | 11.64 | 12.69 | 12.63 | 12.08 | 11.97 | 11.66 | 10.79 |
| | 400 | 8.42 | 8.07 | 7.76 | 8.71 | 8.44 | 8.12 | 8.08 | 7.80 | 7.70 |
| | 600 | 6.41 | 5.94 | 5.60 | 6.45 | 5.99 | 5.77 | 5.72 | 5.71 | 5.58 |

TABLE 22-continued

| Zx/Zy | | Blood Sample A | Blood Sample B | Blood Sample C |
|---|---|---|---|---|
| Glucose | 50 | 1.121 | 1.176 | 1.307 |
| Concentration | 100 | 1.069 | 1.142 | 1.240 |
| (mg/dl) | 250 | 1.048 | 1.050 | 1.109 |
| | 400 | 1.085 | 1.073 | 1.049 |
| | 600 | 1.145 | 1.118 | 1.025 |

As shown in Table 2, the maximum fluctuation width of the value of $Z_x/Z_y$ in Example 21 was in the range exceeding 17%.

Example 22

Various electric current responses were measured in the same manner as in video Example 6 except that a sensor chip in which the capillary part had a width of 1.0 mm and a length of 3.0 mm was used. Table 23 indicates the numerical values (Z and $Z_x/Z_y$) obtained from each blood sample.

TABLE 23

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 41.74 | 40.93 | 38.70 | 40.20 | 38.76 | 35.42 | 31.37 | 30.24 | 26.26 |
| Concentration | 100 | 25.64 | 25.50 | 24.50 | 25.90 | 25.53 | 23.43 | 22.00 | 20.99 | 18.44 |
| (mg/dl) | 250 | 11.85 | 12.02 | 11.78 | 12.11 | 12.50 | 12.07 | 11.36 | 11.36 | 10.65 |
| | 400 | 7.81 | 7.89 | 7.79 | 8.15 | 8.28 | 8.24 | 7.71 | 7.79 | 7.56 |
| | 600 | 5.77 | 5.52 | 5.44 | 5.80 | 5.78 | 5.72 | 5.32 | 5.43 | 5.38 |

| Zx/Zy | | Blood Sample A | Blood Sample B | Blood Sample C |
|---|---|---|---|---|
| Glucose | 50 | 1.079 | 1.135 | 1.195 |
| Concentration | 100 | 1.047 | 1.105 | 1.193 |
| (mg/dl) | 250 | 1.006 | 1.003 | 1.067 |
| | 400 | 1.003 | 0.989 | 1.020 |
| | 600 | 1.061 | 1.014 | 0.989 |

As shown in Table 2, the maximum fluctuation width of the value of $Z_x/Z_y$ in Example 22 was in the range exceeding 17%.

Example 23

Various electric current responses were measured in the same manner as in Example 6 except that a sensor chip in which the capillary part had a height of 0.15 mm was used. Table 24 indicates the numerical values (Z and $Z_x/Z_y$) obtained from each blood sample.

TABLE 24

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 85.32 | 82.96 | 77.51 | 79.47 | 74.73 | 67.59 | 58.91 | 55.71 | 47.46 |
| Concentration | 100 | 53.83 | 53.46 | 50.33 | 52.89 | 50.24 | 45.80 | 43.43 | 39.33 | 34.87 |
| (mg/dl) | 250 | 25.52 | 25.57 | 25.27 | 25.86 | 26.11 | 24.71 | 23.19 | 22.80 | 20.47 |
| | 400 | 16.88 | 17.14 | 16.89 | 17.28 | 17.50 | 17.04 | 15.77 | 15.92 | 15.57 |
| | 600 | 11.84 | 11.82 | 11.65 | 11.95 | 12.11 | 11.96 | 11.03 | 11.24 | 10.99 |

TABLE 24-continued

| Zx/Zy | | Blood Sample A | Blood Sample B | Blood Sample C |
|---|---|---|---|---|
| Glucose | 50 | 1.101 | 1.176 | 1.241 |
| Concentration | 100 | 1.070 | 1.155 | 1.245 |
| (mg/dl) | 250 | 1.010 | 1.047 | 1.133 |
| | 400 | 0.999 | 1.014 | 1.013 |
| | 600 | 1.016 | 0.999 | 1.004 |

As shown in Table 2, the maximum fluctuation width of the value of $Z_x/Z_y$ in Example 23 was in the range exceeding 17%.

Example 24

Various electric current responses were measured in the same manner as in Example 4 except that a sensor chip in which the capillary part had a height of 0.15 mm was used. Table 25 indicates the numerical values (Z and $Z_x/Z_y$) obtained from each blood sample.

TABLE 25

| | | Blood Sample A | | | Blood Sample B | | | Blood Sample C | | |
|---|---|---|---|---|---|---|---|---|---|---|
| Z | | 17° C. | 25° C. | 33° C. | 17° C. | 25° C. | 33° C. | 17° C. | 25° C. | 33° C. |
| Glucose | 50 | 50.07 | 53.61 | 54.99 | 41.71 | 45.83 | 48.88 | 26.69 | 32.36 | 33.49 |
| Concentration | 100 | 33.35 | 35.65 | 36.40 | 30.48 | 32.00 | 33.41 | 21.70 | 23.68 | 26.41 |
| (mg/dl) | 250 | 16.75 | 17.48 | 18.24 | 15.63 | 17.11 | 17.61 | 12.63 | 14.43 | 14.71 |
| | 400 | 11.45 | 11.90 | 12.08 | 10.78 | 11.64 | 12.05 | 8.92 | 9.99 | 10.87 |
| | 600 | 8.41 | 8.40 | 8.41 | 7.63 | 8.18 | 8.52 | 6.46 | 7.10 | 7.57 |

| Zx/Zy | | Blood Sample A | Blood Sample B | Blood Sample C |
|---|---|---|---|---|
| Glucose | 50 | 0.911 | 0.853 | 0.797 |
| Concentration | 100 | 0.916 | 0.912 | 0.822 |
| (mg/dl) | 250 | 0.918 | 0.888 | 0.859 |
| | 400 | 0.948 | 0.895 | 0.821 |
| | 600 | 1.000 | 0.896 | 0.853 |

As shown in Table 2, the maximum fluctuation width of the value of $Z_x/Z_y$ in Example 24 was in the range exceeding 17%.

INDUSTRIAL APPLICABILITY

In the measurement of the analyte concentration in a blood sample, the present invention prevents a measurement error caused by the temperature of the environment where measurement is carried out from occurring and therefore has a great utility value in respective fields having a need for an improvement in measurement accuracy.

The invention claimed is:

1. A biosensor system, comprising:
a measuring instrument having an operation part; and
a sensor chip that is insertable into and removable from the measuring instrument, and comprises a capillary part that retains a blood sample introduced into the sensor chip,
wherein the sensor chip comprises
a measurement part A including an electrode A and an electrode B in the capillary part;
a measurement part B including the electrode A and an electrode C in the capillary part,
a reaction reagent layer formed on the electrodes A and B but not on the electrode C, and
a spacer formed on the reaction reagent layer; wherein
the measuring instrument does not include an environmental temperature measurement part for measuring the environmental temperature;
the measurement part A acquires Data a related to a concentration of an analyte in the blood sample based on the amount of electric current that flows in the blood sample due to a reaction in which an oxidoreductase with the analyte used as a substrate is involved;
the measurement part B acquires Data b suitable for temperature correction of the Data a;
the operation part is configured to determine the concentration of the analyte in the blood sample based on the Data a, as corrected based on the Data b measured by measurement part B, thereby avoiding the influence of the temperature of the blood sample in the measurement of the analyte concentration.

2. The biosensor system according to claim 1, wherein the electrodes A, B and C are formed of conductive materials selected from a group consisting of palladium, platinum, gold, silver, titanium, copper, nickel and carbon.

3. The biosensor system according to claim 1, wherein the spacer has the capillary part, and the height of the capillary part is 0.05 mm to 0.3 mm.

4. The biosensor system according to claim 1, wherein the measuring instrument has a control circuit that provides the measurement part A with a signal that indicates acquisition of the Data a within a range of at least 0.5 second but less than 2.5 seconds from the time when the blood sample has been introduced into the sensor chip.

5. The biosensor system according to claim 1, wherein the reaction reagent layer contains the oxidoreductase,
the reaction reagent layer contains no water-soluble polymer or contains less than 0.2 mass % of water-soluble polymer, and
the measuring instrument has a control circuit that provides the measurement part A with a signal that indicates acquisition of the Data a within a range of at least 0.5 second but less than 2.5 seconds from the time when the blood sample has been introduced into the sensor chip.

6. The biosensor system according to claim 1, wherein the reaction reagent layer contains the oxidoreductase,
the reaction reagent layer contains at least 0.2 mass % of water-soluble polymer, and
the measuring instrument has a control circuit that provides the measurement part A with a signal that indicates acquisition of the Data a after a lapse of at least 2.5 seconds from the time when the blood sample has been introduced into the sensor chip.

7. The biosensor system according to claim 1, wherein the electrode A is a working electrode for the measurement part A and a counter electrode for the measurement part B.

* * * * *